United States Patent [19]

Shuler

[11] Patent Number: 5,217,479
[45] Date of Patent: Jun. 8, 1993

[54] SURGICAL CUTTING INSTRUMENT

[75] Inventor: Donald K. Shuler, Largo, Fla.

[73] Assignee: Linvatec Corporation, Largo, Fla.

[21] Appl. No.: 655,035

[22] Filed: Feb. 14, 1991

[51] Int. Cl.⁵ ............................................. A61B 17/00
[52] U.S. Cl. ................................... 606/180; 128/751
[58] Field of Search ............... 606/167, 180, 170, 179, 606/132; 30/340, 205, 229, 230; 128/751, 752, 753, 754

[56] References Cited

U.S. PATENT DOCUMENTS

| | | | |
|---|---|---|---|
| 2,574,066 | 11/1951 | See | 30/230 |
| 2,721,555 | 12/1952 | Jenney . | |
| 3,618,611 | 11/1971 | Urban . | |
| 3,732,858 | 5/1973 | Banko | 606/170 |
| 4,167,943 | 9/1979 | Banko | 606/170 |
| 4,368,734 | 1/1983 | Banko . | |

OTHER PUBLICATIONS

Biomed. Eng. (USA), vol. 13, No. 4, (Jul.-Aug. 1979) (Publ. Mar. 1980) "New Biopsy Instruments"-E. I. Aksenova et al.

Primary Examiner—C. Fred Rosenbaum
Assistant Examiner—Manuel Mendez

[57] ABSTRACT

The cutting strength of a rotary surgical cutting instrument is increased by an on-axis bearing contact between the distal end of its rotatable inner member and the interior surface of its outer member. The outer member is provided with a distal cutting aperture angularly oriented to the rotation axis and circumscribed by an oval outer cutting edge. The inner member has two symmetrical rows of straight-sided triangular cutting teeth positioned to cooperate with the outer cutting edge to shear tissue, including bone, disposed in the cutting aperture. A clearance gap between the inner and outer members narrows in width in the region between the teeth and the aperture to prevent severed tissue from lodging between the inner and outer members. The height of the cutting teeth is at least 50% of their width, and 15% to 22% of the outer diameter of the inner member. The straight sides of the teeth converge to crests disposed in a first common longitudinal plane. The teeth are separated by roots disposed in a second plane parallel to the first plane but disposed closer than the first plane to the rotation axis.

28 Claims, 2 Drawing Sheets

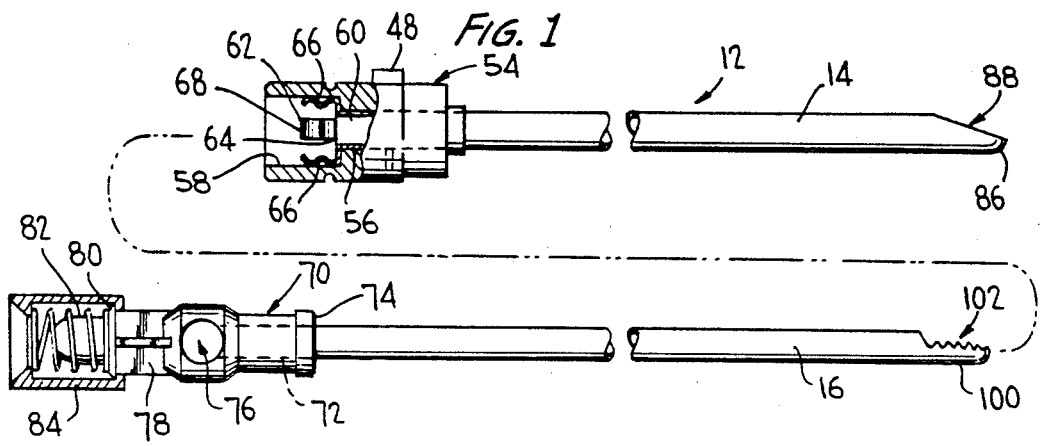
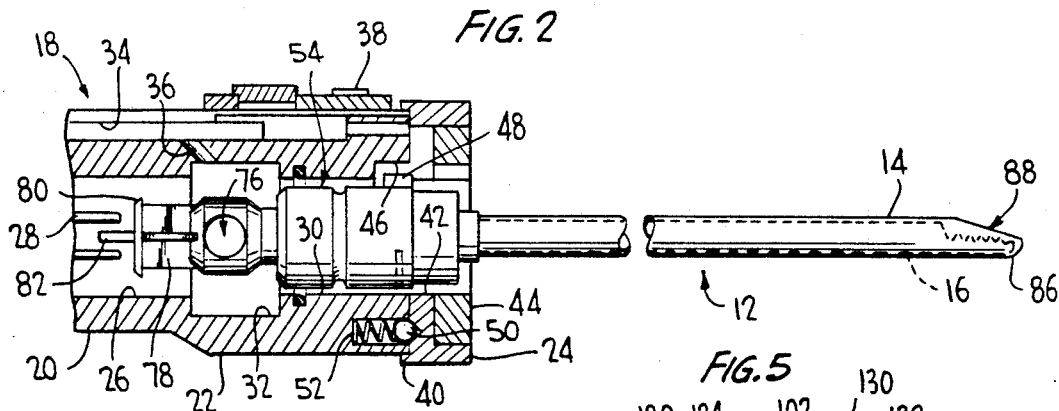
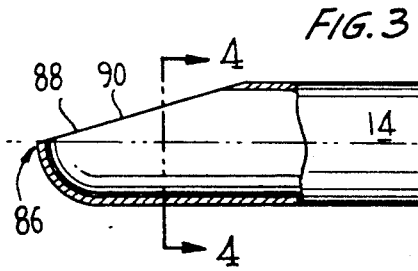
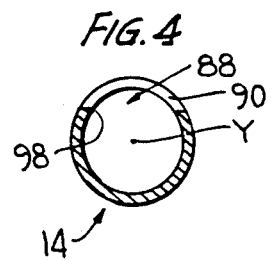
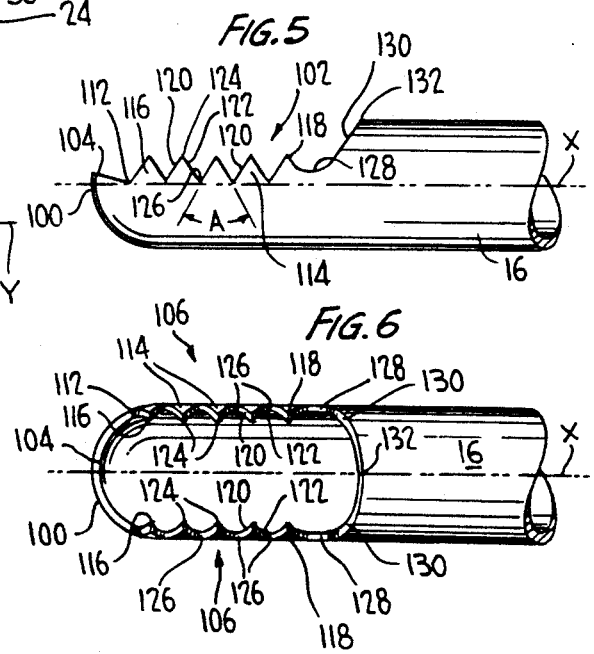

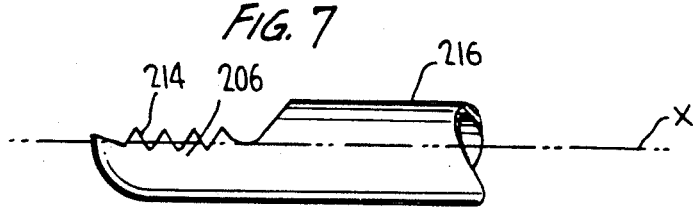
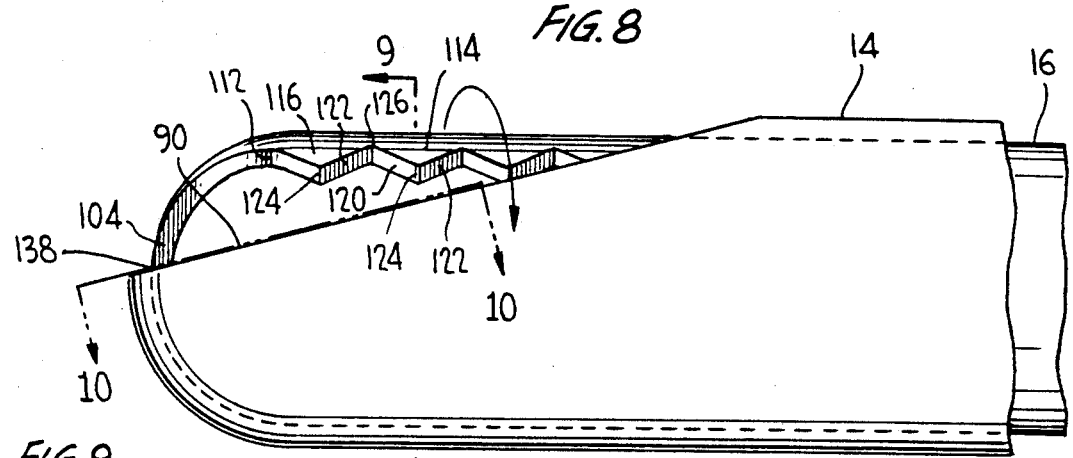
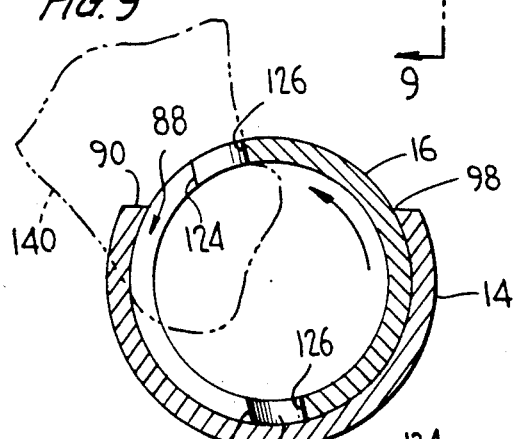
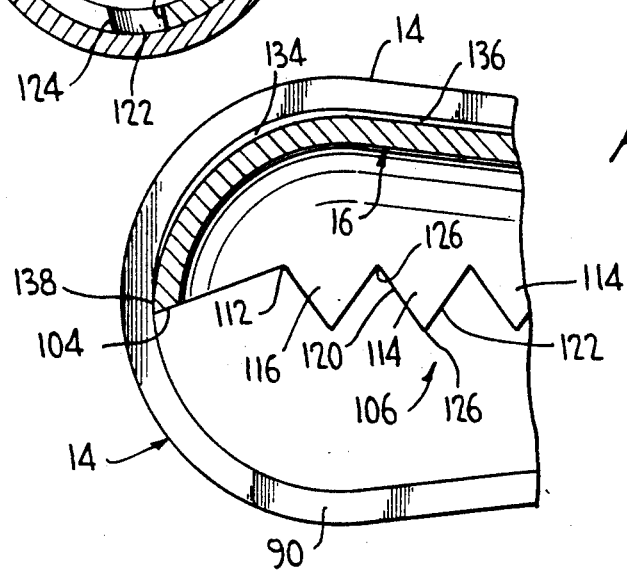

SURGICAL CUTTING INSTRUMENT

BACKGROUND OF THE INVENTION

1. Field Of The Invention

The present invention relates to surgical cutting instruments and, more specifically, to surgical cutting instruments formed of coaxial inner and outer members and having teeth for cutting tissue, including bone. The invention has particular utility in rotatably driven cutting instruments used in arthroscopic surgery.

2. Description Of The Prior Art

It is known in the prior art to provide surgical cutting instruments comprising an outer sleeve with a cutting aperture and a toothed inner tube rotatably mounted within the outer sleeve, permitting the teeth to rotate past the cutting aperture to cut tissue received therein. Examples of cutting instruments of this type are disclosed in U.S. Pat. Nos. 4,368,734 (Banko) and 3,618,611 (Urban). Such instruments possess numerous disadvantages including the relative ineffectiveness of the concavely curved sides of their cutting teeth in cutting tissue. Specifically, when the inner tube is rotated relative to the outer sleeve, the crests of the teeth pierce tissue positioned in the cutting aperture and, as the concave sides of the teeth continue to pass through the tissue, the tissue collects or bunches up in the curved spaces between the teeth. Consequently, the concave-sided teeth cut tissue in a tearing or digging action, rather than with a clean shear cut, the result often being trauma to tissue and the need for relatively long cutting times and high cutting forces to cut even small tissue quantities. Additionally, the height of typical curved cutting teeth is very small in relation to their width and to the diameter of the inner tube, and such shallow teeth are capable of cutting only small increments of tissue for each rotation past the cutting aperture. A further drawback to cutting instruments having teeth with concave sides is that the teeth are formed by overlapping radial machine cuts in the inner tube such that the distance between the origins of the radii of the machine cuts is less than the diameter of their corresponding circles. The overlapping radial machine cuts remove substantial quantities of material from the inner tube, resulting in a substantial reduction in the tube strength. The concavely curved cutting teeth, therefore, generally lack the structural integrity required to apply high cutting forces required to cut bone, or to tolerate impact forces arising from incidental contact with other instruments at the surgical site.

Other surgical cutting instruments of the general type described but having straight-sided cutting teeth are disclosed in U.S. Pat. No. 2,721,555 (Jenny) and in an article by Aksenova et al entitled "New Biopsy Instruments", published in Biomedical Engineering (Vol. 13, No. 4). However, these instruments are generally limited to cutting small fragments of easily penetrable tissue, such as skin and other delicate tissue, due to the cutting teeth being formed as very fine serrations. More particularly, the height of the straight-sided cutting teeth is typically very small in relation to their width and to the diameter of the inner tube and, therefore, the effective cutting length of the cutting edge presented by the straight-sided cutting teeth is only slightly larger than the axial length of the inner member segment along which the teeth are defined. Accordingly, the straight-sided teeth generally cut relatively small amounts of tissue for each rotation past the cutting aperture, require relatively long cutting times to cut tissue, and are defined in a relatively weak structure so as to be precluded from use in surgical procedures necessitating high cutting forces that might break or damage the relatively fragile inner member.

The structural configuration, limited cutting effectiveness and minimal strength of presently available curved and straight-sided cutting teeth typically limit instruments utilizing these cutting teeth to specific cutting functions and types of tissue. Such instruments cannot be employed, for example, to perform multiple, diverse cutting functions, such as resecting, trimming, side cutting, whiskering, burring and the like, on diverse types of tissue including relatively elastic tissue as well as relatively hard tissue, such as bone. The functional limitations of such instruments make it necessary to utilize many specialized cutting instruments in surgical procedures, such as arthrosopy, involving multiple, diverse cutting operations on different types of tissue, thereby adding significantly to the time and complexity of these procedures.

A further drawback shared by surgical cutting instruments of the type described is that a gap is usually maintained between the outer sleeve and the inner tube to permit the inner tube to freely rotate within the outer sleeve without friction and the attendant and potentially damaging heat. This gap, however, is typically wide enough adjacent the cutting teeth for tissue to be drawn therein. Tissue is thusly caught between the outer sleeve and the rotating inner tube and, when the inner tube is rotated at high speeds, the tissue becomes wrapped around the inner tube. When this occurs, rotation of the inner tube is impeded and sometimes totally blocked, requiring time and attention to be diverted from the surgical procedure to free the caught tissue. Moreover, the gap between the inner and outer tubes tends to promote misalignment between these tubes when cutting forces are imposed between them. Since there is no structure in the gap to preserve positional stability of the inner tube, the resulting misalignment impairs the cutting efficiency and effectiveness of the surgical instrument.

OBJECTS AND SUMMARY OF THE INVENTION

Accordingly, it is a primary object of the present invention to overcome the above-mentioned disadvantages associated with prior art cutting instruments having curved or straight-sided cutting teeth.

It is another object of the invention to provide a surgical cutting instrument having cutting teeth capable of performing diverse cutting operations on different types of tissue, including bone.

A further object of the invention is to provide a surgical cutting instrument having cutting teeth formed in a rotatable tube capable of applying large cutting forces.

An additional object of the invention is to provide a surgical cutting instrument having a rotatable inner member carrying cutting teeth capable of cutting relatively large quantities of tissue during each rotation of the inner member.

Yet another object of the invention is to provide a surgical cutting instrument of the type described wherein the effective cutting length provided by cutting teeth is significantly longer then in prior art instruments.

It is also an object of the invention to prevent misalignment between the toothed rotating inner member and the outer tubular member in a surgical cutting instrument of the type described.

A still further object of the invention is to prevent tissue from being trapped or jammed between a toothed cutting edge on a rotating inner member and a cutting edge on an apertured outer tubular member coaxially receiving the inner member.

Among the advantages of the surgical cutting instrument of the present invention over the prior art are: reduced time required to surgically cut tissue; increased strength of the cutting teeth resulting from minimizing the quantity of material removed from the inner member in forming teeth edges; minimization of damaging frictional heat from high speed rotation of the inner member within the outer member; and elimination of the need for multiple specialized cutting instruments to effect different types of cuts in certain surgical procedures, in particular, arthroscopic procedures.

These and other objects, benefits and advantages are achieved with the surgical cutting instrument of the present invention as characterized by an outer tubular member including a proximal end and a distal end with a cutting aperture for receiving tissue, and a coaxially received inner tubular member including a proximal end and a toothed distal end for cutting tissue. The inner member distal end includes a distal cutting edge segment angularly joined to toothed cutting edge segments disposed symmetrically along opposite sides of the inner member. The distal end of the inner member contacts the inner surface of the outer member distal end at a single bearing contact point on the rotation axis to positionally stabilize and support the inner member and prevent misalignments between the members. Each toothed cutting edge segment includes a plurality of longitudinally aligned cutting teeth extending proximally from the distal cutting edge segment. The cutting teeth are defined by straight sides converging at coplanar crests, and joined by coplanar roots, the plane of the roots being parallel to the plane of the crests but located closer to the longitudinal axis (i.e., the rotation axis) of the inner member. The location of these planes is such that at least 80% of the height of each cutting tooth extends into the semi-cylindrical side of the inner member from which most of the material has been removed to form the teeth. In addition, the height of the teeth is at least 50% of their width and on the order of 5% to 22% of the inner member diameter. Respective concave transition segments join the toothed cutting edge segments to the distal leading cutting edge segment. Respective rearward concave sides of the most proximal teeth serve as transitions to inclined edge segments extending from a centered proximal edge segment. The cutting aperture in the outer member is circumscribed by a cutting edge formed by cutting a section in a plane positioned angularly with the central longitudinal axis of the outer member. A clearance gap between the inner and outer members is interrupted only by the single bearing contact point. The gap has a predetermined width but tapers to a relatively narrow width between the edge of the cutting aperture and the cutting teeth to prevent tissue from being drawn between the cutting aperture and the teeth and becoming wrapped around the inner member.

Other objects and advantages of the present invention will become apparent from the following description of the preferred embodiments taken in conjunction with the accompanying drawings.

BRIEF DESCRIPTION OF THE DRAWINGS

FIG. 1 is a broken, exploded side view, partly in section, of the surgical cutting instrument according to the present invention.

FIG. 2 is a broken side view, partly in section, of the surgical cutting instrument of FIG. 1 with a handpiece drive unit.

FIG. 3 is a broken side view, partly in section, of the distal end of the outer tubular member of the surgical cutting instrument of FIG. 1.

FIG. 4 is a view in section of the outer tubular member taken along line 4—4 of FIG. 3.

FIG. 5 is a broken side view of the distal end of the inner tubular member of the surgical cutting instrument of FIG. 1.

FIG. 6 is a broken, top view of the distal end of the inner tubular member of the inner tubular member of the surgical cutting instrument of FIG. 1.

FIG. 7 is a broken side view of the distal end of an alternative embodiment of an inner tubular member of the surgical cutting instrument according to the present invention.

FIG. 8 is a broken side view of the distal end of the surgical cutting instrument according to the present invention showing the inner tubular member being rotated with respect to the outer tubular member.

FIG. 9 is a view in section of the surgical cutting instrument taken along line 9—9 of FIG. 8.

FIG. 10 is a view in section of the surgical cutting instrument taken along line 10—10 of FIG. 8.

DESCRIPTION OF THE PREFERRED EMBODIMENTS

As shown in FIGS. 1 and 2, a surgical cutting instrument 12 according to the present invention includes an elongate outer tubular member 14 and an elongate inner tubular member 16 rotatably disposed within the outer member 14. The surgical cutting instrument 12 is particularly configured to be received in and driven by a handpiece drive unit 18 having a distal end shown in FIG. 2. Handpiece drive unit 18 is the handpiece of the Concept Model 9950 INTRA-ARC Drive System, and reference is made thereto for more specific detail relating to the structure and operation of the handpiece. The handpiece drive unit 18 is described herein only to the extent required to understand the operation of the surgical cutting instrument 12.

Handpiece drive unit 18 includes a generally cylindrical body 20 having an enlarged forward end 22 sealed by a locking ring 24, a longitudinally extending cylindrical bore having a rearward bore section (now shown) for housing a drive motor, an intermediate bore section 26 receiving a drive shaft 28 rotatably driven by the drive motor, a forward bore section 30 receiving the proximal end of the surgical cutting instrument 12, and an aspirating chamber 32 positioned between the intermediate bore section 26 and the forward bore section 30. The aspirating chamber 32 communicates with a vacuum source (not shown) via suction channels 34 and 36 formed in the body 20. A plurality of push-button switches 38 are disposed on the handpiece drive unit 18 to control operation of the drive motor.

Locking ring 24 includes an exposed forward-facing surface, a rearward facing surface abutting the forward end 22 of body 20 and an annular lip 40 extending axially over a short length of the forward end 22. A circular recess in the forward facing surface is disposed concentrically about a central aperture 42, and two arcuate channels are defined through the locking ring within the recess equally spaced from a slot therein and disposed symmetrically about aperture 42. Each channel subtends approximately 90° of arc at a constant radial distance from the center of aperture 42. A disc-shaped spacer 44 is disposed in the locking ring recess and has a central aperture aligned with the aperture 42. Spacer 44 is secured via screws to body 20, the screws passing through the two respective arcuate channels to permit the locking ring 24 to be rotated relative to the spacer 44 and the body 20, limited by the arcuate lengths of the channels (i.e., 90°). Spacer 44 also has a slot extending axially therethrough to a prescribed radial depth from the central aperture, such that when the spacer slot is rotatably aligned with the slot in the locking ring 24 and with a slot 46 in the forward bore section 30, a locator stub 48 on the proximal end of the surgical cutting instrument 12 can freely pass into and out of the handpiece drive unit 18.

The rearward-facing surface of the locking ring 2 includes an arcuate ramp surface extending approximately 140° from the slot along the outer edge of the aperture 42 to serve as a camming surface for inserting the proximal end of the surgical cutting instrument 12 into the handpiece drive unit 18. In one extreme rotational position of the locking ring 24, the slot in the locking ring 24 is aligned with the slot in the spacer 44 and with the slot 46 in the forward bore section 30, whereby the surgical cutting instrument 12 can be inserted through the locking ring 24 sufficiently far that an open end thereof slides over the forward end of the drive shaft 28, and the locator stub 48 is disposed in slot 46 with just a small portion of the stub projecting partially into the locking ring slot. If the locking ring 24 is then rotated 90° to its other extreme position, the camming surface gradually forces the locator stub 48, and with it the surgical cutting instrument 12, rearwardly to produce positive engagement with the drive shaft 28. The two extreme positions of the locking ring 24 are maintained by a detent ball 50 and a spring 52 located in a recess in the forward end 22 of the body 20. The detent ball and spring 52 cooperate with two dimples formed at 90° spaced locations in the rearward-facing surface of the locking ring 24 to provide stops at the two extreme rotational positions of the locking ring. In order to remove the surgical cutting instrument 12 from the handpiece drive unit 18, the locking ring 24 is rotated 90° in the opposite direction to its initial extreme position. When the slot in the locking ring 24 becomes aligned with the spacer slot 44 and the slot 46, the surgical cutting instrument 12 can be easily removed from the handpiece drive unit.

A hub 54 is mounted on a proximal end 56 of the outer tubular member 14, the hub 54 being made of plastic or metal and having a generally cylindrical configuration with the locator stub 48 extending radially therefrom to be received in the slots in the handpiece drive unit 18 as described above. Hub 54 includes a cylindrical recess 58 defined in its proximal end in communication with a distally extending central bore 60 for receiving the proximal end 56 of the outer member 14. A spring 62 is disposed in recess 58 and includes four equally spaced arms extending radially from a central aperture 64 along the bottom of recess 58 and bent to extend proximally along the cylindrical side wall of the recess. One pair 66 of opposing spring arms has curved inwardly bent ends to engage the inner member 14, while the other pair of opposing spring arms 68 has square outwardly bent ends to hold the spring 62 in place in the recess 58.

A hub 70 is secured to the proximal end 72 of the inner tubular member 16 and has a bevelled front lip 74 received in recess 58 in hub 54 of outer member 14 so as to be held in place by spring arms 66. The proximal end 72 of inter tubular member 16 is secured in and extends through an axial bore in hub 70 to communicate with a passage 76 extending diametrically through hub 70 to be disposed in the aspirating chamber 32 in handpiece drive unit 18. A pair of radial ribs 78 is positioned rearwardly of the passage 76 and extend longitudinally to a chamfered lip 80 carrying a rearwardly projecting driven tang 82 adapted to be received in drive shaft 28. A sleeve 84 is telescopically mounted over ribs 78 and drive tang 82, and is spring biased away from lip 80. As illustrated in FIG. 2, wherein sleeve 84 is not shown, inner member 16 is rotatably driven within the outer member 14 by drive shaft 28 engaging the driven tang 82, while suction is produced in the inner member 16 via the channels 34 and 36 communicating with the vacuum source and passage 76. Although the surgical cutting instrument of the present invention is shown and described for use in the Concept INTRA-ARC system, it will be appreciated that the surgical cutting instrument of the present invention can have any desired hub configuration to be utilized with any drive system or handpiece capable of rotating an elongate inner tubular member within an elongate outer tubular member to cut or otherwise engage bodily tissue at the distal end.

The outer tubular member 14 is preferably made of a length of stainless steel tubing having the proximal end 56 adhesively secured in bore 60 of hub 54, and a distal end 86 configured as a segment of a hemisphere and having an aperture or opening 88 defined therein to form a cutting port or window. As shown in FIGS. 3 and 4, orifice 88 is formed by taking a section through a plane inclined at an angle of approximately 15° to the longitudinal axis Y of outer member 14 and intersecting that axis slightly forward of distal end 86 of that member. Orifice 88 is thus circumscribed by a flat edge 90 of generally elliptical configuration. The width of edge 90 in determined by the thickness of tubular member 14 in the inclined section plane. Edge 90 thereby defines a sharp cutting edge corner 98 at its intersection with the inner surface of outer member 14. The cutting edge corner 98 is thus contained in a plane disposed at the acute section angle with central longitudinal axis Y of outer tubular member 14.

The inner tubular member 16 is preferably formed of a length of stainless steel cylindrical tubing having its proximal end 72 adhesively secured in hub 70. The distal end 100 of member 16 is in the form of a segment of a hemisphere and includes a cutting edge 102 rotatable past cutting edge corner 98 on outer member 14 to engage and cut tissue positioned in aperture 88 when inner member 16 is rotatably driven within the outer member 14 by drive shaft 28. As shown in FIGS. 5 and 6, cutting edge 102 is formed by cutting away part of the distal end of member 16 and includes a distal segment 104 arcuately configured and joined at its ends to side segments 106 extending longitudinally along respective opposite sides of the inner member 16. Distal edge segment 104 is an exposed arcuate edge of distal end 100 and is displaced laterally from the central longitudinal axis X of member 16 (i.e., slightly above that axis as viewed in FIG. 5). The opposite ends of distal edge segment 104 are co-planar and taper in a proximal direction toward axis X at an angle of approximately 15. Side edge segments 106 extend from respective ends of distal edge segment 104 and are each formed as a series of longitudinally aligned cutting teeth including distal tooth 116, proximal tooth 118 and intermediate teeth 114, all of generally triangular configuration. Each tooth 114, 116, 118 is laterally aligned with a corresponding tooth on the opposite side edge segment 106. A smooth concave transition 112 between the tapering distal edge segment 104 and the most distal tooth 116 in each series has a radius of curvature significantly smaller than the height (i.e., along the tube circumference) and width (i.e., along the tube length) of the adjacent most distal tooth 116. Each cutting tooth 114, 116, 118 is defined by straight forward and rearward sides 120 and 122, respectively, converging symmetrically at an angle A to a crest 124. All of crests 124 are disposed in a first common plane. The forward and rearward sides of adjacent teeth similarly intersect at respective roots 126 located in a second common plane. The crest plane and root plane are parallel to one another and to the axis X of inner member 16. The plane of roots 126 is disposed closer to axis X than is the plane of crests 124 whereby at least 80% (and preferably 90% or more) of the height of the teeth are disposed on the same hemispherical side of axis X from which material has been cut away to form the teeth. With this configuration the tubular inner member 16 is circumferentially continuous at said crests over an arc in excess of 180°. In addition, the height of the teeth is no less than 50% of their width between roots 126 and, preferably, is between 60% and 70% of the width. The rearward side 128 of the most proximal tooth 118 is arcuate and defined by a radius of curvature considerably larger than the radius of curvature of distal transition segment 112. Rearward side 128 merges smoothly into a straight forward-facing edge segment 130 inclined at substantially the same angle from axis X as the forward sides 120 of teeth 114. Segment 130 extends to a proximal edge segment 132 joining the two side segments 106 and disposed on the same side of axis X as distal segment 104.

As best illustrated, in FIG. 10, an annular clearance gap 134 is provided between the outer surface of the inner member 16 and the inner surface of the outer member 14 to permit high speed rotation of the inner member within the outer member without frictional engagement and the resulting heat that might damage the cutting instrument 12. Gap 134 extends substantially the entire length of outer and inner members 14 and 16; however, the gap clearance tapers to reduced width sections 136 extending longitudinally along both side segments 106 of cutting edge 102 (i.e., in the region of the teeth 114, 116 and 118). The gap clearance 134 also tapers to a contact point 138 at the facing distal ends of the outer and inner tubular members 14 and 16. Specifically, the inner surface of the distal end of outer tubular member 14 contacts the outer surface of distal end 100 of inner tubular member 16, and the bearing contact point 138 resides on the coaxially disposed central longitudinal axes X and Y (i.e., the axis of rotation).

Preferably, angle A formed by the sides of cutting teeth 114, 116 and 118, is in the range of 66° to 77°; the height of the cutting teeth 114, 116 and 118 measured as the distance between the plane of crests 124 and the plane of roots 126, is in the range of 15% to 22% of the outer diameter of inner member 16; edge segments 130 define an angle of 50° to 60° with respect to the central longitudinal axis X of inner member 16; the longitudinal plane containing roots 126 is at or close to axis X, whereas the plane containing the crests 124 is more remote from that axis, so that between 90% and 100% height of teeth 114, 116, 118 reside on the semi-cylindrical side of the axis toward which the teeth generally point; the plane containing edge 90 and edge corner 98 on the outer member 14 defines an angle of approximately 15° with respect to the central longitudinal axis Y of the outer member; and the width of gap 134 is approximately 0.0005 inches and the width of the narrowed width sections 136 is approximately 0.00025 inches.

Although the side cutting edge segments 106 are depicted in FIG. 5 as including five cutting teeth on each side, the exact number of teeth can vary in accordance with the diameter of inner member 16, there being fewer cutting teeth provided on smaller diameter inner members. As shown in FIG. 7, a relatively small diameter inner tubular member 216 includes four cutting teeth 214 on each side segment 206.

The relative proportions and configurations described herein produce numerous advantages. The straight configuration for the forward and rearward facing tooth sides 120 and 122 strengthens the cutting teeth 114, 116, 118 by minimizing the quantity of metal material that must be removed from inner member 16 to form the teeth. In addition, the straight tooth sides effect a shearing action as opposed to tearing the tissue. The straight forward and rearward facing tooth sides are effective in cutting tissue, including bone, for the entire height of the cutting teeth, and the crest angle A provides effective shear cutting in both relatively soft and hard tissue. The specified range of heights of the cutting teeth relative to the outer diameter of the inner tubular member 16, and the range of tooth heights relative to tooth widths, provides structurally strong cutting teeth. The strong cutting teeth minimize tooth breakage and enable the teeth to shear large quantities of tissue during each passage of a cutting edge side region 106 past the aperture 88. The location of the plane containing roots 126 proximate the central longitudinal axis X of the inner member 16 further increases the strength of the cutting end of member 16 by providing a larger structural support than is present when little or no part of the teeth project into the semicylindrical region opposite the support structure for the teeth. The angular orientations of the distal edge segment 104, concave transitions 112, arcuate segments 128 and the forward-facing segments 130 are selected to further minimize the quantity of metal material removed from the inner member 16 during machining and, thereby, enhance the structural integrity of that member. The angular orientation of edge 90 and its corner 98 relative to axis Y of outer member 14 reduces the amount of material removed from the outer member and thusly strengthens that member while providing controlled, sequential cutting of tissue when one of the side edge segments 106 is rotated past the cutting edge corner 98. The distal contact point 138 supports and positionally stabilizes the inner tubular member 16 as it rotates in outer tubular member 14 to prevent misalignment of the members at high rotation speeds. Contact point 138 serves to further positionally stabilize the inner member 16 when large cutting forces are imposed and, therefore, permits hard tissue, such as bone, to be cut without deforming member 16. The reduced width sections 136 of the clearance gap 134 prevent tissue from being drawn between the members and becoming wrapped around the rotating inner member 16.

In operation, the surgical cutting instrument 12 is inserted into handpiece drive unit 18 in the manner described above and is positioned at the surgical site through a portal for arthroscopic surgery. The speed and operation of the surgical cutting instrument 12 is controlled by switches 38, and the surgeon advances the surgical cutting instrument 12 to position tissue, such as bone and meniscus cartilage, within aperture 88 in outer tubular member 14. As shown in FIG. 8, the inner member 16 is rotatably driven within the outer member 14, such that a portion of the distal cutting edge segment 104 and one of the cutting edge side segments sequentially penetrate and cut tissue when rotated past the cutting edge corner 98. Severed tissue is aspirated through the lumen of the inner tubular member 16 to exit the surgical instrument 12 via the passage 76 communicating with the aspirating chamber 32 in the handpiece drive unit 18. The cutting teeth 114, 116, 118 produce an aggressive cutting action in tissue, including bone, and the converging forward and rearward facing tooth sides 120 and 122 cut tissue in a shearing action rather than a tearing or digging type of cut. As shown in FIG. 9, the crests 126 of the straight-sided, triangular shaped teeth pierce and grip tissue 140 positioned in the outer member aperture 88, and pull the tissue into such opening as the inner member 16 rotates. The forward and rearward facing sides 120 and 122 of the teeth continue to cut through the tissue 140 in a shearing action as the teeth move across the opening 88. The surgical cutting instrument 12 possesses the ability to perform diverse cutting operations on both soft and hard tissue that would normally necessitate the use of diverse, specialized cutting blades. For example, the surgical cutting instrument 12 can be utilized as a full radius resector, a synovial resector, a trimmer, a meniscus cutter, a side cutter, a whisker, an arthroplasty burr, and the like, for cutting, shaping and finishing bone surfaces as well as other types of tissue.

Having described a preferred embodiment of a new and improved surgical cutting instrument constructed in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A surgical cutting instrument for cutting anatomical tissue comprising
    an elongate outer tubular member having a proximal end, a distal end and a longitudinal axis;
    cutting port means at said distal end for receiving anatomical tissue;
    an elongate inner tubular member having a proximal end and a distal end;
    tissue cutting means on said inner member distal end including a plurality of straight-sided triangular cutting teeth linearly aligned parallel with said axis; and
    mounting means for securing said inner member coaxially within said outer member to permit selective rotation of said inner member relative to said outer member, wherein the distal end of said inner member is in engagement with the distal end of said outer member, and wherein said cutting means is positioned to cut anatomical tissue received through said cutting port means when said inner member is rotated in said outer member.

2. A surgical cutting instrument as recited in claim 1 wherein the distal end of said outer member includes an end wall having an outer surface and an arcuate inner surface;
    wherein the distal end of said inner member is an end wall having an arcuate outer surface; and
    wherein said engagement of said distal ends comprises a bearing contact, on said longitudinal axis, between said arcuate inner surface and said arcuate outer surface.

3. A surgical cutting instrument for cutting tissue comprising
    an elongate outer tubular member having a proximal end, a distal end and an outer cutting edge at said distal end;
    an elongate inner tubular member having a central longitudinal axis, a proximal end, a distal end and an inner cutting edge at said distal end, said inner cutting edge defining a plurality of triangular cutting teeth each having straight linear sides converging to a crest, said inner member being coaxially and rotatably received in said outer member to position said inner cutting edge adjacent said outer cutting edge and to permit said inner cutting edge to move past said outer cutting edge to cut tissue; and
    a clearance gap disposed between said inner and outer members, said gap having a predetermined width tapering to a relatively narrow width between said outer cutting edge and said inner cutting edge.

4. A surgical cutting instrument as recited in claim 3 wherein said clearance gap extends longitudinally between said inner member and said outer member from said distal ends to said proximal ends.

5. A surgical cutting instrument as recited in claim 4 wherein said outer cutting edge extends longitudinally on said outer member and said inner cutting edge extends longitudinally on said inner member.

6. A surgical cutting instrument as recited in claim 5 wherein said crests are disposed in a first common plane extending longitudinally of said inner member, wherein said teeth are separated by a series of roots disposed in a second common plane oriented parallel to said first plane and closer than said first plane to said longitudinal axis.

7. A surgical cutting instrument for cutting anatomical tissue comprising
    an elongate outer tubular member having a proximal end, a distal end, an inner surface and a longitudinal axis;
    an opening at said distal end circumscribed by a planar edge disposed angularly with said axis and intersecting said inner surface;
    an elongate inner tubular member rotatably received in said outer member and having a proximal end, a distal end and a longitudinal axis; and
    tissue cutting means at said inner member distal end including an arcuate leading cutting edge segment angularly disposed with respect to said inner member longitudinal axis, and first and second toothed cutting edge segments joined to respective opposite ends of said leading cutting edge segment, said toothed cutting edge segments being symmetrically disposed about said longitudinal axis and including a plurality of cutting teeth each having straight sides converting to a crest, wherein said inner member at corresponding crests of said first and second toothed cutting edge segments is circumferentially continuous over an arc in excess of 180°, said cutting means being positionable adjacent said opening to cut anatomical tissue through said opening when said inner member is rotated in said outer member.

8. A surgical cutting instrument as recited in claim 7 wherein said cutting edge teeth in each toothed cutting segment are linearly aligned on said inner member in a series of teeth extending longitudinally from said leading cutting edge segment toward the proximal end of said inner member.

9. A surgical cutting instrument as recited in claim 8 wherein said cutting teeth are joined by roots disposed in a first longitudinally extending plane disposed proximate said inner member longitudinal axis, and wherein the crests of said cutting teeth are disposed in a plane oriented parallel to the plane containing said roots but more remote from the longitudinal axis of said inner member.

10. A surgical cutting instrument as recited in claim 9 wherein said converging sides define an angle at said crests of approximately 66° to 77°.

11. A surgical cutting instrument as recited in claim 9 wherein the distance between said first and second planes is approximately 15% to 22% of the outer diameter of said inner member.

12. A surgical cutting instrument as recited in claim 9 wherein the distance between said first and second planes is at least 50% of the spacing between successive roots.

13. A surgical cutting instrument as recited in claim 9 wherein said forward-facing cutting edge segment is disposed at an angle of approximately 50° to 60° with said inner member longitudinal axis.

14. A surgical cutting instrument as recited in claim 13 wherein the planar edge circumscribing said opening is contained in a plane disposed at an angle of approximately 14° to 16° with said outer member longitudinal axis.

15. A surgical cutting instrument as recited in claim 9 wherein said toothed cutting edge segments each include a most proximal cutting tooth joined to respective ends of a proximal arcuate cutting edge segment.

16. A surgical cutting instrument as recited in claim 15 wherein said proximal arcuate cutting edge segment is disposed on the inner member on the same side of the inner member relative to the inner member longitudinal axis as the plane containing said crests.

17. A surgical cutting instrument as recited in claim 16 wherein said inner member includes a generally forward-facing cutting edge segment disposed angularly with respect to said inner member longitudinal axis, and wherein said proximal arcuate cutting edge segment is joined to said forward-facing cutting edge segment.

18. A surgical cutting instrument as recited in claim 17 wherein said leading cutting edge segment is joined to said toothed cutting edge segment by a distal curved edge segment.

19. A surgical cutting instrument as recited in claim 18 wherein said forward facing cutting edge segment converges distally at an acute angle toward said inner member longitudinal axis.

20. A surgical cutting instrument for cutting anatomical tissue comprising
an elongate outer tubular member having a proximal end, a distal end and a longitudinal axis, said distal end including an end wall having an outer surface and an arcuate inner surface;
cutting port means at said distal end for receiving anatomical tissue;
an elongate inner tubular member having a proximal end and a distal end, said inner member distal end being an end wall having an arcuate outer surface;
tissue cutting means on said inner member distal end including a plurality of straight-sided triangular cutting teeth linearly aligned parallel with said axis; and
mounting means for securing said inner member coaxially within said outer member to permit selective rotation of said inner member relative to said outer member, wherein said inner member distal end is in engagement with said outer member distal end, said engagement comprising a bearing contact, on said longitudinal axis, between said arcuate inner surface and said arcuate outer surface, said bearing contact being the only contact between said inner and outer members distally of said proximal end of said outer member, and wherein said cutting means is positioned to cut anatomical tissue received through said cutting port means when said inner member is rotated in said outer member.

21. A surgical cutting instrument for cutting anatomical tissue comprising
an elongate outer tubular member having a proximal end, a distal end and a longitudinal axis, said distal end including an end wall having an outer surface and an arcuate inner surface;
cutting port means at said distal end for receiving anatomical tissue;
an elongate inner tubular member having a proximal end and a distal end, said inner member distal end being an end wall having an arcuate outer surface;
tissue cutting means on said inner member distal end including a plurality of straight-sided triangular cutting teeth linearly aligned parallel with said axis;
mounting means for securing said inner member coaxially within said outer member to permit selective rotation of said inner member relative to said outer member, wherein said inner member distal end is in engagement with said outer member distal end, said engagement comprising a bearing contact, on said longitudinal axis, between said arcuate inner surface and said arcuate outer surface, and wherein said cutting means is positioned to cut anatomical tissue received through said cutting port means when said inner member is rotated in said outer member; and
a clearance gap between said inner and outer members totally surrounding said bearing contact.

22. A surgical cutting instrument as recited in claim 21 wherein said clearance gap has a predetermined width throughout except for a relatively narrow width proximate said tissue cutting means to prevent severed tissue from being drawn into said gap.

23. A surgical cutting instrument as recited in claim 22 wherein said narrow width is approximately one-half said predetermined width.

24. A surgical cutting instrument as recited in claim 23 wherein said predetermined width is approximately 0.0005 inches and said narrow width is approximately 0.00025 inches.

25. A surgical cutting instrument for cutting tissue comprising an elongate outer tubular member having a proximal end, a distal end and an outer cutting edge at said distal end, said outer cutting edge extending longitudinally on said outer member;

an elongate inner tubular member having a central longitudinal axis, a proximal end, a distal end and an inner cutting edge at said distal end, said inner cutting edge extending longitudinally on said inner member, said inner cutting edge defining a plurality of triangular cutting teeth each having straight linear sides converging to a crest, said inner member being coaxially and rotatably received in said outer member to position said inner cutting edge adjacent said outer cutting edge and to permit said inner cutting edge to move past said outer cutting edge to cut tissue; and a clearance gap disposed between said inner and outer members, said gap extending longitudinally between said inner and outer members from said distal ends to said proximal ends and having a predetermined width tapering to a relatively narrow width between said outer cutting edge and said inner cutting edge, said narrow width being approximately one-half said predetermined width.

26. A surgical cutting instrument as recited in claim 25 wherein said predetermined width is approximately 0.0005 inches and said narrow width is approximately 0.00025 inches.

27. A surgical cutting instrument for cutting tissue comprising an elongate outer tubular member having a proximal end, a distal end and an outer cutting edge at said distal end, said outer cutting edge extending longitudinally on said outer member;

an elongate inner tubular member having a central longitudinal axis, a proximal end, a distal end, a predetermined outer diameter and an inner cutting edge at said distal end, said inner cutting edge extending longitudinally on said inner member, said inner cutting edge defining a plurality of triangular cutting teeth each having straight linear sides converging to a crest, said crests being disposed in a first common plane extending longitudinally of said inner member, said teeth being separated by a series of roots disposed in a second common plane oriented parallel to said first plane and closer than said first plane to said longitudinal axis, said teeth having a height measured between said first and second planes that is at least 15% of said outer diameter, said inner member being coaxially and rotatably received in said outer member to position said inner cutting edge adjacent said outer cutting edge and to permit said inner cutting edge to move past said outer cutting edge to cut tissue; and a clearance gap disposed between said inner and outer members, said gap extending longitudinally between said inner member and said outer member from said distal ends to said proximal ends and having a predetermined width tapering to a relatively narrow width between said outer cutting edge and said inner cutting edge.

28. A surgical cutting instrument for cutting tissue comprising an elongate outer tubular member having a proximal end, a distal end and an outer cutting edge at said distal end, said outer cutting edge extending longitudinally on said outer member;

an elongate inner tubular member having a central longitudinal axis, a proximal end, a distal end and an inner cutting edge at said distal end, said inner cutting edge extending longitudinally on said inner member, said inner cutting edge defining a plurality of triangular cutting teeth each having straight linear sides converging to a crest, said crests being disposed in a first common plane extending longitudinally of said inner member, said teeth being separated by a series of roots disposed in a second common plane oriented parallel to said first plane and closer than said first plane to said longitudinal axis, said teeth having a height measured between said first and second planes and a width measured between said roots, said height being in the range of 60% to 70% of said width, said inner member being coaxially and rotatably received in said outer member to position said inner cutting edge adjacent said outer cutting edge and to permit said inner cutting edge to move past said outer cutting edge to cut tissue; and a clearance gap disposed between said inner and outer members, said gap extending longitudinally between said inner member and said outer member from said distal ends to said proximal ends and having a predetermined width tapering to a relatively narrow width between said outer cutting edge and said inner cutting edge.

* * * * *

UNITED STATES PATENT AND TRADEMARK OFFICE
CERTIFICATE OF CORRECTION

PATENT NO. : 5,217,479
DATED : June 8, 1993
INVENTOR(S) : Donald K. Shuler

It is certified that error appears in the above-identified patent and that said Letters Patent is hereby corrected as shown below:

Column 3, line 49, change "5%" to --15%--.

Column 5, line 23, change "2" to --24--.

Column 7, line 4, change "15" to --15%--.

Signed and Sealed this

Twenty-second Day of February, 1994

*Attest:*

BRUCE LEHMAN

*Attesting Officer*    *Commissioner of Patents and Trademarks*